United States Patent [19]
Schoelling

[11] Patent Number: 5,533,966
[45] Date of Patent: Jul. 9, 1996

[54] TAMPON APPLICATOR, ESPECIALLY FOR FEMININE HYGIENE

[75] Inventor: Hans W. Schoelling, Ennepetal, Germany

[73] Assignee: McNeil-PPC, Inc., Milltown, N.J.

[21] Appl. No.: 255,837

[22] Filed: Jun. 7, 1994

Related U.S. Application Data

[63] Continuation of Ser. No. 647,878, Jan. 30, 1991, abandoned.

[30] Foreign Application Priority Data

Feb. 1, 1990 [DE] Germany .......................... 40 02 975.1

[51] Int. Cl.⁶ ................................................... A61F 13/32
[52] U.S. Cl. ................................................. 604/18; 604/904
[58] Field of Search ................................. 604/1–3, 11–18, 604/904

[56] References Cited

U.S. PATENT DOCUMENTS

| | | | |
|---|---|---|---|
| 3,015,332 | 1/1962 | Brecht | 128/263 |
| 3,124,134 | 3/1964 | Gardner | 604/904 |
| 3,347,234 | 10/1967 | Voss | 128/260 |
| 3,643,661 | 2/1972 | Crockford | 128/263 |
| 3,696,812 | 10/1972 | Jaycox | 128/263 |
| 3,760,808 | 9/1973 | Bleuer | 604/14 |
| 3,835,856 | 9/1974 | Warncke | 128/263 |
| 4,286,595 | 9/1981 | Ring | 604/904 |
| 4,291,696 | 9/1981 | Ring | 604/14 |
| 4,329,991 | 5/1982 | Sakurai | 604/16 |
| 4,411,647 | 10/1983 | Sakurai et al. | 604/16 |
| 4,424,054 | 1/1984 | Conn et al. | 604/11 |
| 4,447,222 | 5/1984 | Sartinoranont | 604/15 |
| 4,479,791 | 10/1984 | Sprague | 604/14 |
| 4,498,899 | 2/1985 | Gross | 604/16 |
| 4,536,178 | 8/1985 | Lichstein et al. | 604/15 |
| 4,676,773 | 6/1987 | Sheldon | 604/14 X |
| 4,857,044 | 8/1989 | Lennon | 604/14 |
| 4,891,042 | 1/1990 | Melvin et al. | 604/18 |
| 4,921,474 | 5/1990 | Suzuki et al. | 604/16 |
| 4,960,417 | 10/1990 | Tarr, Jr. et al. | 604/15 |

FOREIGN PATENT DOCUMENTS

| | | |
|---|---|---|
| 0291343A1 | 11/1988 | European Pat. Off. . |
| 91101301 | 5/1991 | European Pat. Off. . |
| 91117744 | 2/1992 | European Pat. Off. . |
| 3910458 | 9/1990 | Germany ........................... 604/11 |
| WO82/02489 | 8/1982 | WIPO . |
| 9011747 | 10/1990 | WIPO ............................. 604/14 |

*Primary Examiner*—Mary Beth Jones
*Assistant Examiner*—Dennis Ruhl

[57] ABSTRACT

An inner sleeve (12) and an outer sleeve (11) of a tampon applicator provided especially for feminine hygiene form a one-part injection moulding in order to simplify production and assembly. The rear end of the outer sleeve (11) and the front end of the inner sleeve (12) are connected by means of a predetermined breaking point (13). The predetermined breaking point (13) is destroyed due to axial pressure, so that the inner sleeve (12) can be pushed into the outer sleeve (11).

10 Claims, 2 Drawing Sheets

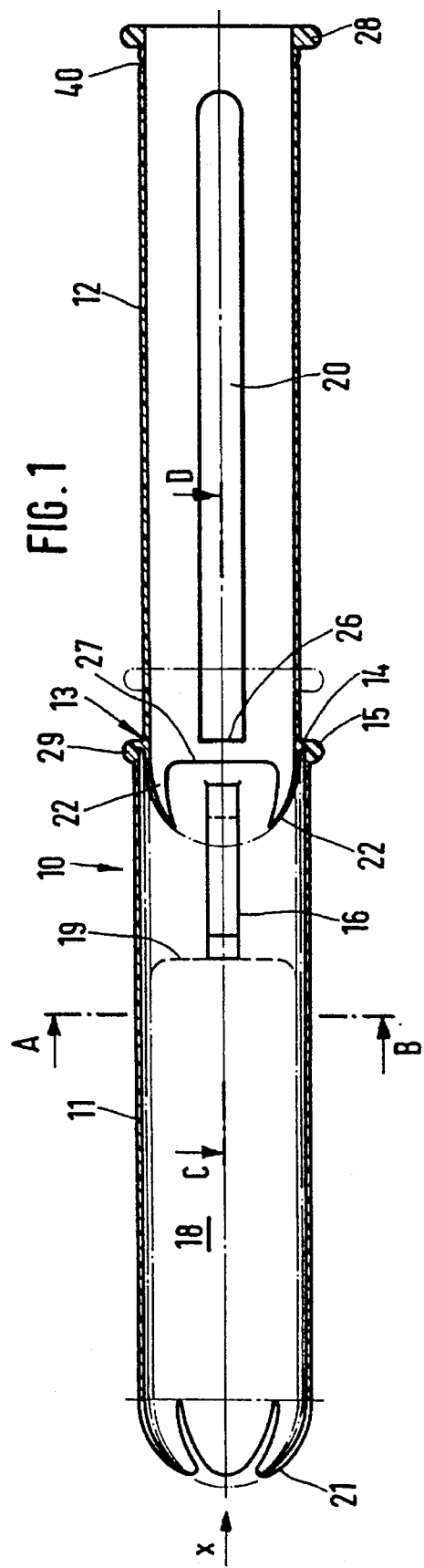
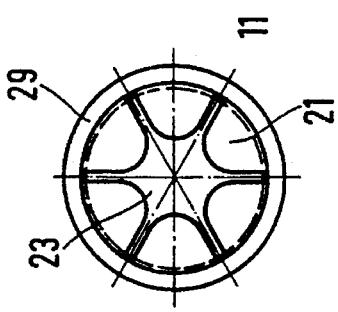
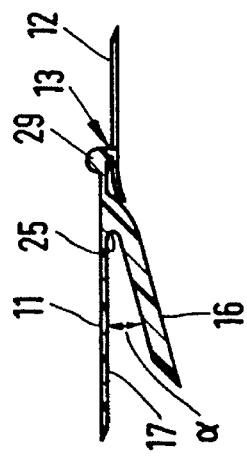
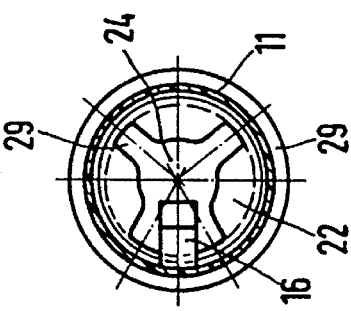

FIG. 5
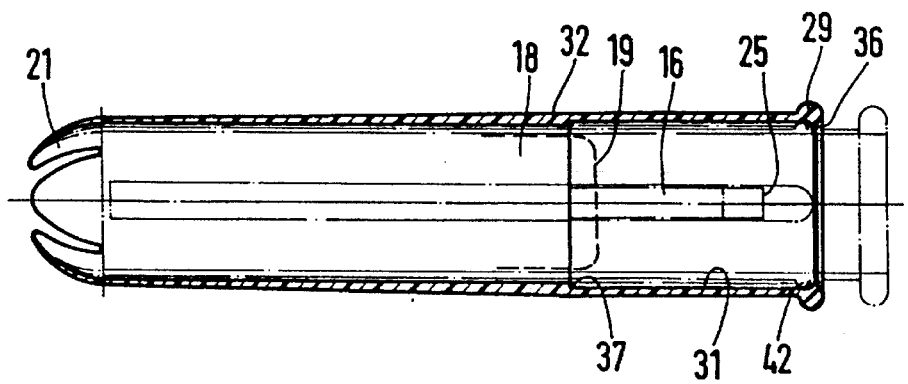
FIG. 6
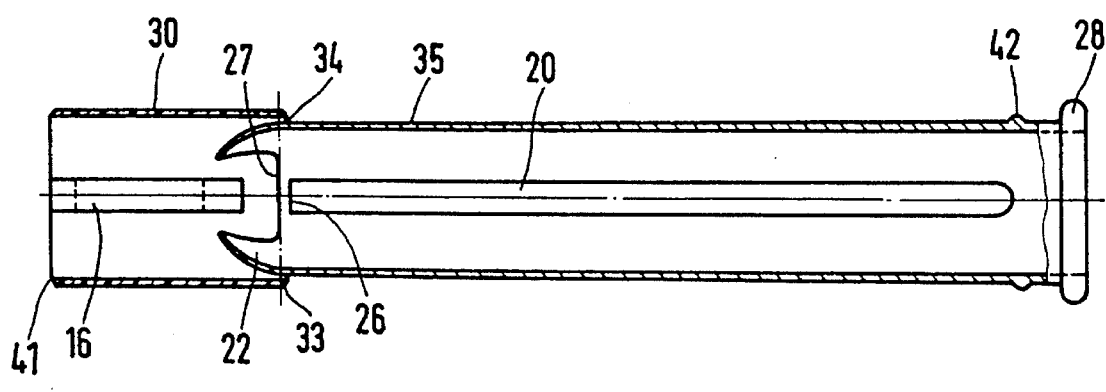
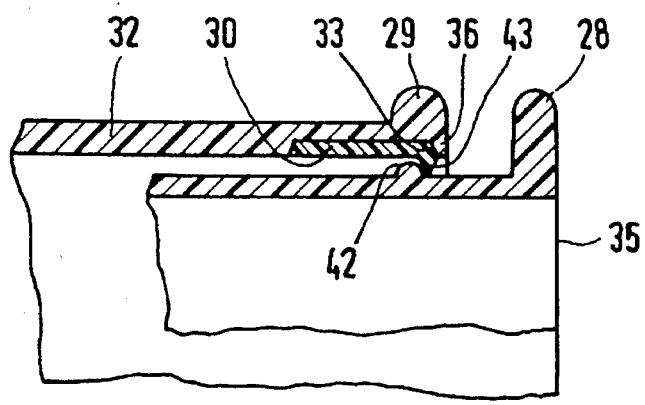
FIG. 7

5,533,966

TAMPON APPLICATOR, ESPECIALLY FOR FEMININE HYGIENE

This is a continuation of application Ser. No. 07/647,878, filed Jan. 30, 1991, now abandoned.

FIELD OF THE INVENTION

The present invention relates to a tampon application, especially for feminine hygiene, having a cylindrical outer sleeve and a cylindrical inner sleeves which is displaceable therein. The outer sleeve has a tongue-shaped elastic tampon catch to transfer a tampon from the inner sleeve to the outer sleeve for ultimate discharge from the applicator.

BACKGROUND OF THE INVENTION

Tampon applicators of this generic type are known from German Utility Models 74 42 182 or G 89 03 946.7 or from U.S. Pat. No. 4,286,595. These known tampon applicators consist of plastic and require the production of at least two injection mouldings, for which at least two injection-moulding machines or two separate injection moulds are needed when conventional methods are used. Furthermore, the joining together of the injection mouldings (assembly of the tampon applicator by pushing the inner sleeve into the outer sleeve) necessitates an expensive assembly machine, by means of which the radial alignment of the tampon catch on the inner wall of the outer sleeve in relation to the longitudinal slot of the inner sleeve has to be ensured. Furthermore, in known tampon applicators, constructive measures are taken to make it certain that the inner sleeve, after being pushed into the outer sleeve, cannot fall out of the latter. These measures involve a special outlay for tools.

The object on which the invention is based is to improve the tampon applicator of the generic type described in the pre-characterizing clause, in such a way that the outlay in terms of production and assembly is reduced, that is to say the assembly machine is simplified or can even be omitted, and at the same time the radial alignment of the tampon catch in relation to the longitudinal slot in the inner sleeve is guaranteed and the inner sleeve is prevented from falling out of the outer sleeve when the inner sleeve is pushed into the outer sleeve.

SUMMARY OF THE INVENTION

The present invention relates to a tampon applicator having a cylindrical outer sleeve and a cylindrical inner sleeve which is displaceable therein. The outer sleeve has a tongue-shaped elastic tampon catch to transfer a tampon from the inner sleeve to the outer sleeve for ultimate discharge from the applicator. The inner sleeve is equipped with a longitudinal slot which is closed at its front and rear ends. There are elastic lips tapering in a forward direction from roots at the front end of both the outer sleeve and the inner sleeve. The lips curve inwardly toward the center longitudinal axis of the tampon applicator. A tampon is initially surrounded by the inner sleeve, but the tampon is transferred from the inner sleeve to the outer sleeve during manipulation of the applicator for its ultimate discharge from the applicator. The inner sleeve also has a grip at its rear end to allow a user to grasp the inner sleeve and withdraw it almost completely from the rear end of the outer sleeve.

During the withdrawal of the inner sleeve from the outer sleeve, a tongue-shaped elastic tampon catch transfers the tampon into the outer sleeve. The tampon catch is connected integrally to The outer sleeve adjacent its rear end and projects through the longitudinal slot of the inner sleeve into its interior. At least a part of the outer sleeve, equipped with the tampon catch, is integrally formed from plastic with the inner sleeve. The inner sleeve and the portion of the outer sleeve which is equipped with the tampon catch are connected to one another by means of at least one predetermined breaking point between the rear end of that part of the outer sleeve and the front end of the inner sleeve. The tampon catch is aligned radially with the longitudinal slot in the inner sleeve, and the at least one predetermined breaking point consists of plastic skin which extends from the rear end of the outer sleeve to the front end of the inner sleeve in a region between the roots of the lips of the inner sleeve and the front end of the longitudinal slot.

In another embodiment, the outer sleeve can be formed completely of plastic, and the tampon applicator can be produced from a one-part injection moulding. There is therefore no need for an assembly machine for inserting the inner sleeve into the outer sleeve and for aligning the tampon catch in relation to the longitudinal slot in the inner sleeve. It is also necessary to have only one injection-moulding machine or injection mould for producing the injection moulding.

According to a second embodiment of the invention, that part of the outer sleeve consisting of plastic and equipped with the tampon catch can be designed as a cylindrical insert which is injection-moulded from plastic in one part with the inner sleeve and which can be inserted into and fixed in a rear length portion of widened diameter of the outer sleeve. It is thereby possible to produce the main part of the outer sleeve from paper or cardboard.

The predetermined breaking point appropriately consists of a plastic skin or of a number of plastic webs which extends from the rear end of the outer sleeve/of the insert to the front cylindrical end of the inner sleeve in the region between the lip roots of the latter and the front end of the longitudinal slot. In order to push the inner sleeve into the outer sleeve of the applicator or fill the applicator with the tampon to obtain the shortened transport form, the predetermined breaking point is destroyed by means of axial pressure. The residues of the predetermined breaking point which remain on the outer sleeve perform the function of preventing the inner sleeve from creeping out during its transport. Thus, as a result of the destruction of the predetermined breaking point, the outer sleeve and inner sleeve or the outer-sleeve insert and inner sleeve are thus formed respectively from the one-part injection moulding. These two parts are connected to one another, to form a slide system retained at the front and rear, as a result of the axial coincidence of the tampon catch in the outer sleeve with the longitudinal slot in the inner sleeve.

Additionally, to secure the insert in the outer sleeve, on the inside of the rear widening of the outer sleeve there can be at least one catch bead or catch segment which engages with a catching effect behind the rear end of the insert inserted into the outer sleeve.

Furthermore, it is recommended to have the arrangement of at least one detent element on the outside of the rear end of the inner sleeve at an axial distance in front of the grip, designed as an annular bead, for the radially inwardly projecting residual edge of the destroyed predetermined breaking point at the rear and of the outer sleeve or of the insert. This ensures that the inner sleeve maintains its position pushed completely into the outer sleeve and can be pulled out of the outer sleeve only by overcoming a slight resistance, before the tampon applicator is to be used for introducing the tampon into the body cavity.

The invention is described in detail below by means of the diagrammatic drawing of two exemplary embodiments of a tampon applicator.

BRIEF DESCRIPTION OF THE DRAWING

FIG. 1 shows a longitudinal mid-section through a one-part tampon applicator produced completely from plastic;

FIG. 2 shows a cross-section A–B according to FIG. 1;

FIG. 3 shows a longitudinal section C–D according to FIG. 1;

FIG. 4 shows a view X of the front end of the outer sleeve of the applicator of FIG. 1;

FIG. 5 shows a longitudinal mid-section through the outer sleeve of a second embodiment of a tampon applicator, and FIG. 6 shows a longitudinal mid-section through the inner sleeve of the second embodiment of the tampon applicator;

FIG. 7 shows the outer sleeve and inner sleeve in an interlocked position according to FIG. 6.

DETAILED DESCRIPTION OF THE PREFERRED EMBODIMENTS

FIGS. 1 to 4 illustrate a tampon applicator 10 for feminine hygiene, which consists of a one-part plastic injection moulding. The tampon applicator 10 is composed of an essentially cylindrical outer sleeve 11 and of an essentially cylindrical inner sleeve 12 with an outside diameter which is smaller than the inside diameter of the outer sleeve 11.

The outer sleeve 11 and the inner sleeve 12 are connected to one another by means of a predetermined breaking point 13, so that the two parts can be produced as a one-part injection moulding on a single plastic injection-moulding machine or in one injection mould. The predetermined breaking point 13 can consist of a plastic skin 14 which extends over 360° of the applicator circumference and which connects the rear end face 15 of the outer sleeve 11 to the front end of the cylindrical part of the inner sleeve 12. Alternatively, the plastic skin 14 can be provided only on circumferential portions of the applicator. If appropriate, the predetermined breaking point can also be made spot-shaped or web-shaped. The predetermined breaking point 13 is located in the region of the closed front end 26 of the longitudinal slot 20 or of the lip root 27 of the lips 22 of the inner sleeve 12.

A tampon catch 16 resembling a spring clip is attached to the inner wall 17 of the outer sleeve 11 at an axial distance from the rear end face 15 of the outer sleeve 11 and extends in a plane which is radial relative to the longitudinal mid-axis of the outer sleeve 11 and at an acute angle e to the front end of the outer sleeve 11. The length of the tampon catch 16 is calculated so that, in the inner sleeve 12, represented by dot-and-dash lines, within the outer sleeve 11, a tampon 18 indicated by dot-and-dash lines in FIG. 1 bears with its rear end 19 against the pointed end of the tampon catch 16 and is fixed in its axial position by this.

As is evident, the inner sleeve 12 is equipped with an axial longitudinal or guide slot 20, closed at the front and rear, which by means of the predetermined breaking point 13 is aligned coaxially with and at a distance from the tampon catch 16 and which is dimensioned wider than this. Consequently, by exerting axial pressure on the inner sleeve 12, the predetermined breaking point 13 can be destroyed and the inner sleeve 12 pushed into the outer sleeve 11 so that the tampon catch 16 is first bent back against the inner wall 17 of the outer sleeve 11 by the inner sleeve 12, before it automatically engages radially into the longitudinal slot 20. Subsequently, the tampon 18 can be pushed from the rear end, past the tampon catch 16, into the inner sleeve 12 pushed into the outer sleeve 11 and into the position represented by dot-and-dash lines in FIG. 1, so that it is surrounded coaxially by the inner sleeve 12.

The production of the one-part injection moulding according to FIG. 1 is accompanied at the same time by the shaping of forwardly tapered, elastic and in each case outwardly curved lips 21 at the front end of the outer sleeve 11 and lips 22 at the front end of the inner sleeve 12. The lips 21, 22 are respectively designed as segments of a hemisphere and are rounded at their edges, their ends leaving a relatively large central orifice 23 and 24 (FIG. 2 and 4) free. A pair of the lips 22 of the inner sleeve 12 engages at a distance round the starting point 25 of the tampon catch 16. The lips 22 of the inner sleeve 12 likewise serve for fixing the tampon 18 axially and are assisted in this by the lips 21 of the outer sleeve.

The inner sleeve 12 is equipped, at the rear end, with a grip bead 28 for grasping the inner sleeve 12 and pulling it approximately completely out of the rear end of the outer sleeve 11. The end face 15 at the rear end of the outer sleeve 11 is likewise formed by a grip bead 29.

A detent element in the form of an annular groove 40 (FIG. 1) is arranged on the outside of the rear end of the inner sleeve 12 at an axial distance from the grip bead 28 of the latter for a radially inwardly projecting residual edge 43 of the destroyed predetermined breaking point 13 at the rear end of the outer sleeve 11 of the insert 30. This prevents an unintentional displacement of the inner sleeve 12 pushed completely into the outer sleeve 11. Instead of the annular groove 40, an annular or spot-shaped detent projection or detent bead can also be provided, as described below.

In the second embodiment of a tampon applicator in FIGS. 5, 6 and 7 parts identical to the above-described first embodiment bear the same reference symbols. Essentially only those features of the second embodiment which differ from the first embodiment are therefore described below. A part equipped with the tampon catch 16 and consisting of plastic forms a cylindrical insert 30 which can be inserted into a rear length portion 31 of widened diameter of an outer sleeve 32. The rear end 33 of this insert 30 is connected by means of a predetermined breaking point 34 to the front end of the cylindrical portion of an inner sleeve 35 in the region between the lip roots 27 of the latter and the front end 26 of the longitudinal slot 20 closed at the ends. The insert 30 and the inner sleeve 35 therefore constitute a single plastic injection moulding.

An inner annular shoulder 37 limits the widened length portion 31 at the rear end of the outer sleeve 32 and serves as a stop for the front end 41 of the insert 30 during the assembly of the tampon applicator. For fixing the insert 30 in the outer sleeve 32 there is, on the inside of the rear end of the widened length portion 31 of the outer sleeve 32, an annular catch bead 36 which engages with a catching effect behind the rear end 33 of the insert 30 inserted into the outer sleeve 32. When further axial pressure is exerted on the inner sleeve 35 in relation to the outer sleeve 32, the predetermined breaking point 34 between the insert 30 and the inner sleeve 35 is destroyed, so that the latter can be pushed telescopically further into the outer sleeve 32. The outer sleeve 32 can consist of paper or cardboard, if so desired. The diameter of the cylindrical inner wall of the insert 30 corresponds approximately to that of the inner wall of the outer sleeve 32.

In this second embodiment too, the initially axial and subsequently also radial alignment of the tampon catch 16, formed in one part with the insert 30 and the inner sleeve 35, in relation to the longitudinal slot 20 of the inner sleeve 35 is ensured by the predetermined breaking point 34. During the assembly of the insert 30 together with the inner sleeve 35, the elastic tampon catch 16 is bent back by the lip root 27 of the inner sleeve 35; before it then engages radially into the longitudinal slot 20 of the inner sleeve 35 and fixes the latter relative to the outer sleeve 32. The tampon 18 can thereafter be pushed into the inner sleeve 35 positioned in the outer sleeve 32. For this, as in the first embodiment, the tampon 18 presses radially outwards the tampon catch 16 which subsequently moves back into the position shown in FIG. 3 and which takes its place behind the rear end 19 of the tampon 18. Consequently, when the tampon applicator is to be used, the tampon 18 can be transferred into the outer sleeve 32 by pulling the inner sleeve 35 back out of the rear end of the latter and can thereafter be ejected from the outer sleeve 32 by means of the lips 22 of the inner sleeve 35 which are laid against the rear end 19 of the tampon 18. The starting point 25 of the tampon catch 16 (see FIG. 3) is provided at such an axial distance from the rear end of the insert 30 that, according to FIG. 5, in the state in which the inner sleeve 35 is pushed into the outer sleeve 32, the rear end of the longitudinal slot 20 is covered by the outer sleeve 32.

In FIGS. 6 and 7, a detent element for the retention of the inner sleeve 35 is designed as an annular or spot-shaped detent projection or detent bead 42. This detent bead 42 is arranged at such an axial distance from the grip bead 28 that, according to FIG. 7, a residual edge 43 of the predetermined breaking point 34 engages behind the detent bead 42 on the insert 30 and retains the inner sleeve 35 in its position within the outer sleeve 32. Instead of the detent bead 42, the annular groove 40 shown in FIG. 1 can also advantageously be provided.

It is evident that this second embodiment likewise allows savings during the production and assembly of the tampon applicator.

List of reference symbols

| | |
|---|---|
| 10 | Tampon applicator |
| 11 | Outer sleeve |
| 12 | Inner sleeve |
| 13 | Predetermined breaking point |
| 14 | Plastic skin |
| 15 | Rear end face of outer sleeve |
| 16 | Tampon catch |
| 17 | Inner wall |
| 18 | Tampon |
| 19 | Rear end of tampon |
| 20 | Longitudinal slot |
| 21 | Lips of outer sleeve |
| 22 | Lips of inner sleeve |
| 23 | Orifice of outer sleeve |
| 24 | Orifice of inner sleeve |
| 25 | Starting point |
| 26 | Closed front end |
| 27 | Lip root |
| 28 | Grip bead |
| 29 | Grip bead |
| 30 | Insert |
| 31 | Widened length portion |
| 32 | Outer sleeve |
| 33 | Rear end of insert |
| 34 | Predetermined breaking point |

-continued

List of reference symbols

| | |
|---|---|
| 35 | Inner sleeve |
| 36 | Catch bead |
| 37 | Annular shoulder |
| 40 | Annular groove |
| 41 | Frontal end face of insert |
| 42 | Detent bead |
| 43 | Residual edge |

What is claimed is:

1. Tampon applicator, especially for feminine hygiene, comprising:

a cylindrical outer sleeve having an outer sleeve inside diameter and a rear end;

a cylindrical inner sleeve having an interior and an outside and defining a longitudinal axis for the tampon applicator with an outside diameter smaller than the outer sleeve inside diameter, the inner sleeve being mounted coaxially displaceably in the outer sleeve and being equipped with an axial longitudinal slot having a front end, said slot being closed at each of a longitudinal front and rear end of the inner sleeve;

elastic lips tapering in a forward direction from roots at a front end of the outer sleeve and of the inner sleeve, the lips curving inward toward a center longitudinal axis of the tampon applicator;

a tampon which is surrounded coaxially by the inner sleeve;

a grip at the rear end of the inner sleeve for grasping the inner sleeve and pulling it out almost completely from the rear end of the outer sleeve, and at least one detent element is arranged on the outside of the rear end of the inner sleeve at an axial distance from the grip;

a tongue-shaped elastic tampon catch which is connected integrally to the outer sleeve adjacent its rear end and projects through the longitudinal slot of the inner sleeve into its interior and which, when the inner sleeve is being pulled out of the rear end of the outer sleeve, transfers the tampon into the outer sleeve;

wherein (1) at least a part of the outer sleeve is equipped with the tampon catch, (2) the inner sleeve and said part of the outer sleeve which is equipped with the tampon catch are integrally formed from plastic and are connected to one another by means of at least one predetermined breaking point between a rear end of the said part of the outer sleeve and the front end of the inner sleeve, (3) the tampon catch is aligned radially with the longitudinal slot in the inner sleeve, (4) said at least one predetermined breaking point consists of plastic skin which extends from the rear end of the outer sleeve to the front end of the inner sleeve in a region between the roots of the lips of the inner sleeve and the front end of the longitudinal slot, and (5) said detent element is capable of engaging a radially inwardly projecting residual edge formed upon destruction of said at least one predetermined breaking point at the rear end of the outer sleeve to restrict movement of the inner sleeve into the outer sleeve.

2. Tampon applicator according to claim 1, wherein the outer sleeve consists completely of plastic.

3. Tampon applicator according to claim 1, wherein said outer sleeve comprises a front portion having the outer sleeve inside diameter, a rear length portion extending rearwardly from the front portion having a widened diameter and a cylindrical insert, said cylindrical insert forming said part of the outer sleeve which is equipped with the tampon catch and being inserted into the rear length portion.

4. Tampon applicator according to claim 3, wherein the rear end of the rear length portion of the outer sleeve has an inside, and a catch bead disposed on the inside of the rear end engages with the cylindrical insert to secure the cylindrical insert in the outer sleeve.

5. Tampon applicator according to claim 4, wherein the cylindrical insert has an inside diameter corresponding to the outer sleeve inside diameter.

6. Tampon applicator according to claim 5, wherein the cylindrical insert has an inner wall and a front end, and the tampon catch is attached at an axial distance from the rear end of the outer sleeve to the inner wall of the insert and extends into a cross-sectional plane defined by the front end of the insert.

7. Tampon applicator according to claim 4, wherein the outer sleeve receiving the insert consists of paper or cardboard.

8. Tampon applicator according to claim 1, wherein the tampon catch is disposed between a pair of mutually adjacent lips at the front end of the inner sleeve before destruction of the predetermined breaking point.

9. Tampon applicator according to claim 1, wherein the outer sleeve consists of paper or cardboard and is configured to receive an insert.

10. Tampon applicator according to claim 1, wherein the tampon catch is disposed between a pair of mutually adjacent lips at the front end of the inner sleeve before destruction of the predetermined breaking point.

* * * * *